: US010722295B2

United States Patent
Kopp

(10) Patent No.: US 10,722,295 B2
(45) Date of Patent: Jul. 28, 2020

(54) ROBOTIC SURGICAL ASSEMBLIES AND ELECTROSURGICAL INSTRUMENTS THEREOF

(71) Applicant: Covidien LP, Mansfield, MA (US)

(72) Inventor: Brock Kopp, Branford, CT (US)

(73) Assignee: COVIDIEN LP, Mansfield, MA (US)

(*) Notice: Subject to any disclaimer, the term of this patent is extended or adjusted under 35 U.S.C. 154(b) by 323 days.

(21) Appl. No.: 15/548,251

(22) PCT Filed: Jan. 20, 2016

(86) PCT No.: PCT/US2016/014002
§ 371 (c)(1),
(2) Date: Aug. 2, 2017

(87) PCT Pub. No.: WO2016/133631
PCT Pub. Date: Aug. 25, 2016

(65) Prior Publication Data
US 2018/0008338 A1 Jan. 11, 2018

Related U.S. Application Data

(60) Provisional application No. 62/116,664, filed on Feb. 16, 2015.

(51) Int. Cl.
*A61B 18/14* (2006.01)
*A61B 34/30* (2016.01)
(Continued)

(52) U.S. Cl.
CPC .......... *A61B 18/1445* (2013.01); *A61B 34/30* (2016.02); *A61B 34/35* (2016.02);
(Continued)

(58) Field of Classification Search
CPC ....... A61B 18/1442–1447; A61B 2018/00077; A61B 2018/00083; A61B 2018/0063;
(Continued)

(56) References Cited

U.S. PATENT DOCUMENTS 7,722,607 B2  5/2010  Dumbauld et al.
8,506,557 B2  8/2013  Zemlock et al.
(Continued)

FOREIGN PATENT DOCUMENTS

EP   2772206 A2   9/2014
JP   2003310629 A  11/2003
(Continued)

OTHER PUBLICATIONS

European Search Report dated Sep. 6, 2018, corresponding to European Application No. 16752762.1; 11 pages.
(Continued)

*Primary Examiner* — Thomas A Giuliani
*Assistant Examiner* — James A Cipriano
(74) *Attorney, Agent, or Firm* — Carter, DeLuca & Farrell LLP

(57) ABSTRACT

An actuation mechanism for actuating an electrosurgical end effector includes a housing and a shaft assembly extending distally from the housing. The shaft assembly includes an elongate collar, a shaft extending through the elongate collar, and a longitudinal bar axially movable relative to the shaft. The elongate collar has an internal threadform extending along a length thereof. The longitudinal bar includes a proximal end having an extension engaged to the internal threadform of the elongate collar and a distal end configured to be coupled to a knife blade of an electrosurgical end effector. Rotation of the elongate collar axially moves the longitudinal bar relative to the elongate collar to move the knife blade.

19 Claims, 13 Drawing Sheets

(51) Int. Cl.
*A61B 34/35* (2016.01)
*A61B 17/00* (2006.01)
*A61B 90/00* (2016.01)
*A61B 17/29* (2006.01)
*A61B 18/00* (2006.01)

(52) U.S. Cl.
CPC ..... *A61B 17/29* (2013.01); *A61B 2017/00398* (2013.01); *A61B 2017/00477* (2013.01); *A61B 2017/00862* (2013.01); *A61B 2017/2903* (2013.01); *A61B 2017/2936* (2013.01); *A61B 2018/0063* (2013.01); *A61B 2018/00077* (2013.01); *A61B 2018/00083* (2013.01); *A61B 2018/1455* (2013.01); *A61B 2090/034* (2016.02)

(58) Field of Classification Search
CPC ....... A61B 2018/1475; A61B 2018/145–1462; A61B 34/30; A61B 34/35; A61B 2017/00398; A61B 2017/00477; A61B 2017/00862; A61B 2017/2903; A61B 2017/2936; A61B 2017/2902; A61B 2090/034
See application file for complete search history.

(56) References Cited

U.S. PATENT DOCUMENTS

| | | |
|---|---|---|
| 2011/0290856 A1 | 12/2011 | Shelton, IV et al. |
| 2012/0022524 A1 | 1/2012 | Timm et al. |
| 2012/0292367 A1* | 11/2012 | Morgan ............... A61B 17/072 227/175.1 |
| 2013/0041360 A1* | 2/2013 | Farritor ............. A61B 18/1445 606/29 |
| 2013/0123783 A1 | 5/2013 | Marczyk et al. |
| 2013/0131651 A1 | 5/2013 | Strobl et al. |
| 2013/0296848 A1* | 11/2013 | Allen, IV ........... A61B 18/1445 606/41 |
| 2014/0005677 A1 | 1/2014 | Shelton, IV et al. |
| 2014/0175149 A1* | 6/2014 | Smith .................. A61B 90/90 227/175.2 |
| 2014/0252071 A1 | 9/2014 | Moore et al. |

FOREIGN PATENT DOCUMENTS

| | | |
|---|---|---|
| JP | 2013540004 A | 10/2013 |
| JP | 2014523769 A | 9/2014 |
| WO | WO 2012-112888 | 8/2012 |
| WO | 2013048595 A1 | 4/2013 |

OTHER PUBLICATIONS

International Search Report for (PCT/US2016/014002) date of completion is Mar. 21, 2016 (4 pages).

Japanese Office Action (with English translation) dated Aug. 7, 2019, corresponding to counterpart Japanese Application No. 2017-542420; 7 total pages.

Japanese Office Action (with English Summary Form), dated Nov. 14, 2019, corresponding to counterpart Japanese Application No. 2017-542420; 3 total pages.

\* cited by examiner

ROBOTIC SURGICAL ASSEMBLIES AND ELECTROSURGICAL INSTRUMENTS THEREOF

CROSS-REFERENCE TO RELATED APPLICATIONS

This application is a U.S. National Stage Application filed under 35 U.S.C. § 371(a) of International Patent Application Serial No. PCT/US2016/014002, filed Jan. 20, 2016, which claims the benefit of and priority to U.S. Provisional Patent Application Ser. No. 62/116,664, filed Feb. 16, 2015, the entire disclosure of which is incorporated by reference herein.

BACKGROUND

Robotic surgical systems have been used in minimally invasive medical procedures. Some robotic surgical systems include a console supporting a surgical robotic arm and a surgical instrument or at least one end effector (e.g., forceps or a grasping tool) mounted to the robotic arm. The robotic arm provides mechanical power to the surgical instrument for its operation and movement. Each robotic arm may include an instrument drive unit that is operatively connected to the surgical instrument.

Manually-operated surgical instruments often include a handle assembly for actuating the functions of the surgical instrument. However, when using a robotic surgical system, no handle assembly is typically present to carry out the functions of the end effector. Accordingly, to use each unique surgical instrument with a robotic surgical system, the selected surgical instrument may require certain modifications so that the surgical instrument is adapted for use with the robotic surgical system.

SUMMARY

In accordance with an aspect of the present disclosure, an actuation mechanism for actuating an electrosurgical end effector is provided. The actuation mechanism includes a housing and a shaft assembly extending distally from the housing. The shaft assembly includes an elongate collar, a shaft, and a longitudinal bar. The elongate collar has an internal threadform extending along a length thereof. The shaft extends through the elongate collar and has a proximal end and a distal end. The distal end is configured to effectuate movement of a jaw member of an electrosurgical end effector upon axial movement of the shaft relative to the housing. The longitudinal bar is axially movable relative to the shaft and includes a proximal end and a distal end. The proximal end has an extension engaged to the internal threadform of the elongate collar. The distal end is configured to be coupled to a knife blade of an electrosurgical end effector. Rotation of the elongate collar axially moves the longitudinal bar relative to the elongate collar to move the knife blade.

In embodiments, the housing may include a first drive member and a second drive member. The first drive member may be operatively coupled with the elongate collar such that rotation of the first drive member rotates the elongate collar relative to the housing. The second drive member may be operatively coupled with the proximal end of the shaft such that rotation of the second drive member axially moves the shaft relative to the housing. The first drive member may include a gear. The elongate collar may also include a gear, which may be in meshing engagement with the gear of the first drive member.

It is contemplated that the shaft assembly may further include a collar assembly fixedly disposed about the proximal end of the shaft. The housing may further include a shroud threadedly engaged to the second drive member and in abutment with the collar assembly such that axial movement of the shroud, via rotation of the second drive member, results in axial movement of the shaft via axial movement of the collar assembly. In embodiments, the collar assembly may include a proximal collar, a distal collar, and a biasing member. The proximal collar may be fixed to the shaft. The distal collar may be slidably engaged to the shaft. The biasing member may interconnect the proximal collar and the distal collar. The distal collar may define an annular cavity. The shroud may have a protrusion disposed within the annular cavity such that proximal and distal movement of the shroud results in corresponding proximal and distal movement of the collar assembly.

In some embodiments, the shaft assembly may further include a collar assembly disposed about the proximal end of the shaft. The collar assembly may be threadedly engaged to the second drive member such that axial movement of the collar assembly, via rotation of the second drive member, results in axial movement of the shaft.

In some embodiments, the housing may further include a first input drive coupler and a second input drive coupler. The first input drive coupler may be non-rotatably coupled to a proximal end of the first drive member. The second input drive coupler may be non-rotatably coupled to a proximal end of the second drive member.

It is envisioned that the elongate collar may be prevented from moving axially relative to the housing.

It is contemplated that the shaft may include a longitudinal slot formed therein. The extension of the longitudinal bar may be disposed outside of the longitudinal slot such that the shaft and the longitudinal bar are axially movable relative to one another.

In embodiments, the housing may include at least one securement member configured to secure the housing to a surgical robotic arm.

In another aspect of the present disclosure, an electrosurgical instrument is provided. The electrosurgical instrument includes an end effector and an actuation mechanism. The end effector includes a pair of opposing jaw members and a knife blade. The jaw members are configured to grasp and seal a tissue disposed therebetween. The knife blade is movably disposable between the pair of opposing jaw members to sever the tissue disposed therebetween. The actuation mechanism includes a housing and a shaft assembly. The shaft assembly extends distally from the housing. The shaft assembly includes an elongate collar, a shaft, and a longitudinal bar. The elongate collar has an internal threadform extending along a length thereof. The shaft extends through the elongate collar and has a proximal end and a distal end. The distal end is in operative communication with one of the pair of opposing jaw members such that movement of the shaft relative to the housing approximates or expands the pair of opposing jaw members. The longitudinal bar is axially movable relative to the shaft. The longitudinal bar includes a proximal end and a distal end. The proximal end has an extension engaged to the internal threadform of the elongate collar. The distal end is coupled to the knife blade. Rotation of the elongate collar axially moves the longitudinal bar relative to the elongate collar to move the knife blade.

In yet another aspect of the present disclosure, a robotic surgical assembly is provided. The robotic surgical assembly includes a surgical robotic arm, an end effector and an actuation mechanism. The end effector includes a pair of opposing jaw members and a knife blade. The jaw members are configured to grasp and seal a tissue disposed therebetween. The knife blade is movably disposable between the pair of opposing jaw members to sever the tissue disposed therebetween. The actuation mechanism is configured to be coupled to the surgical robotic arm. The actuation mechanism includes a housing and a shaft assembly. The housing includes a first drive member and a second drive member. The shaft assembly extends distally from the housing. The shaft assembly includes an elongate collar, a shaft, and a longitudinal bar. The elongate collar is operatively coupled to the first drive member and has an internal threadform extending along a length thereof. The shaft extends through the elongate collar and has a proximal end operatively coupled to the second drive member and a distal end in operative communication with one of the pair of opposing jaw members such that movement of the shaft relative to the housing via rotation of the second drive member approximates or expands the pair of opposing jaw members. The longitudinal bar is axially movable relative to the shaft and includes a proximal end and a distal end. The proximal end has an extension engaged to the internal threadform of the elongate collar. The distal end is coupled to the knife blade. Rotation of the elongate collar via rotation of the first drive member axially moves the longitudinal bar relative to the elongate collar to move the knife blade.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about +or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
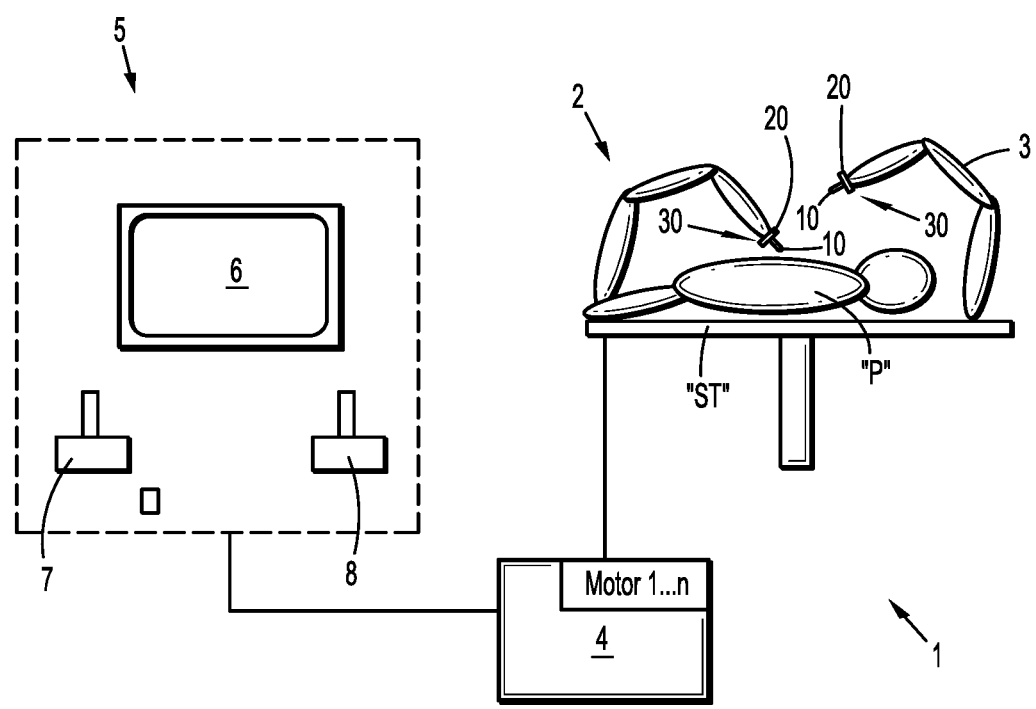
FIG. 1 is a schematic illustration of a robotic surgical system including a robotic surgical assembly in accordance with the present disclosure.

Embodiments of the presently disclosed robotic surgical system including an actuation mechanism for actuating an electrosurgical end effector and methods thereof are described in detail with reference to the drawings, in which like reference numerals designate identical or corresponding elements in each of the several views. As used herein the term "distal" refers to that portion of the robotic surgical system, actuation mechanism, electrosurgical end effector, or component thereof that is further from the user, while the term "proximal" refers to that portion of the robotic surgical system, actuation mechanism, electrosurgical end effector, or component thereof that is closer to the user.

Figure 2:
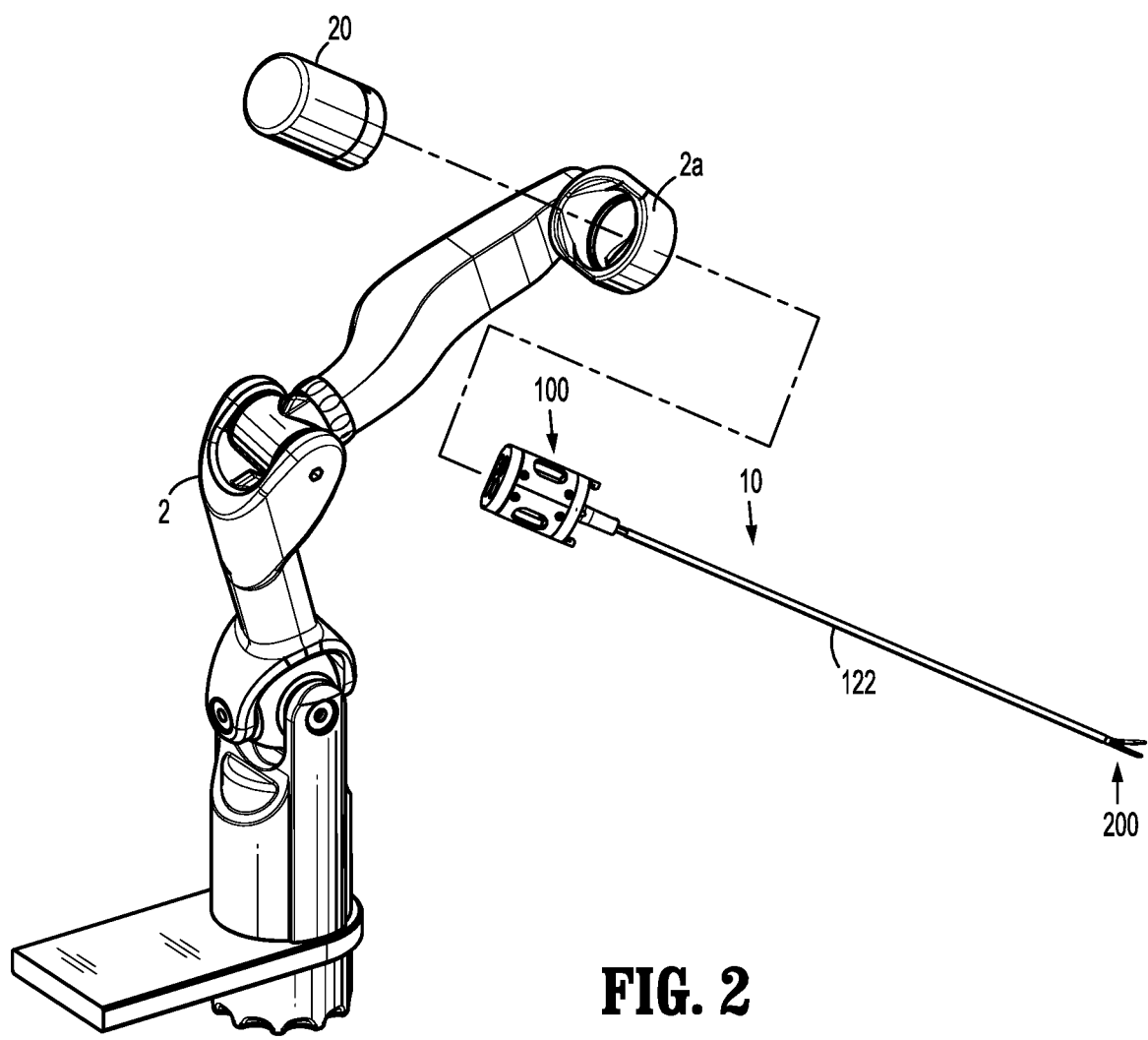
FIG. 2 is a perspective view of a surgical robotic arm of the robotic surgical assembly of FIG. 1 illustrating an electrosurgical instrument and an instrument drive unit being attached to the surgical robotic arm.

Referring initially to FIGS. 1 and 2, a surgical system, such as, for example, a robotic surgical system 1, generally includes a plurality of surgical robotic arms 2, 3 having an electrosurgical instrument 10 removably attached thereto; a control device 4; and an operating console 5 coupled with control device 4.

With continued reference to FIG. 1, operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, their instrument drive units 20, and thus electrosurgical instrument 10 (including electrosurgical end effector 200) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electrosurgical instrument 10. Robotic surgical system 1 may also include more than two robotic arms 2, 3, the additional robotic arms likewise being connected to control device 4 and being telemanipulatable by means of operating console 5. A surgical instrument, for example, electrosurgical surgical instrument 10 (including electrosurgical end effector 200, FIGS. 8A and 8B), may also be attached to the additional robotic arm.

Control device 4 may control a plurality of motors (Motor 1 . . . n) with each motor configured to drive a relative rotation of drive members of an actuation mechanism 100 (FIGS. 2-7) of electrosurgical instrument 10 to effect operation and/or movement of each electrosurgical end effector 200 of electrosurgical instrument 10. It is contemplated that control device 4 coordinates the activation of the various motors (Motor 1 . . . n) to coordinate a clockwise or counter-clockwise rotation of drive members (not shown) of instrument drive unit 20 in order to coordinate an operation and/or movement of a respective electrosurgical end effector 200. In embodiments, each motor can be configured to actuate a drive rod or a lever arm to effect operation and/or movement of each electrosurgical end effector 200 of electrosurgical instrument 10.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated herein by reference.

As will be described in greater detail below, referring momentarily to FIGS. 3A-8B, electrosurgical instrument 10 includes an actuation mechanism 100 and an electrosurgical end effector 200. Actuation mechanism 100 of electrosurgical instrument 10 interfaces with one of the surgical robotic arms 2, 3 and is operatively engaged to electrosurgical end effector 200 to actuate functions of electrosurgical end effector 200 via power delivered by an instrument drive unit 20 (FIG. 2). In particular, as described in greater detail below, actuation mechanism 100 of electrosurgical instrument 10 includes an elongate collar 160 and a longitudinal bar 170 that interact with one another to move, translate, or slide a knife blade 218 of electrosurgical end effector 200 to transect tissue disposed between jaw members 202a, 202b of electrosurgical end effector 200.

With specific reference to FIG. 2, robotic surgical system 1 includes a surgical assembly 30, which includes robotic arm 2, an electrosurgical instrument 10 coupled with or to robotic arm 2, and an instrument drive unit 20 coupled to electrosurgical instrument 10. Instrument drive unit 20 is configured for powering electrosurgical instrument 10. Instrument drive unit 20 transfers power and actuation forces from its motors (not shown) to actuation mechanism 100 of electrosurgical instrument 10 to ultimately drive movement of components of electrosurgical end effector 200, for example, a movement of knife blade 218 (FIG. 8A) and/or a closing and opening of jaw members 202a, 202b (FIGS. 8A and 8B) of electrosurgical end effector 200. Instrument drive unit 20 includes a plurality of driving members (not shown) attached to a respective motor (not shown) such that the drive members are independently rotatable with respect to one another.

Figure 3A:
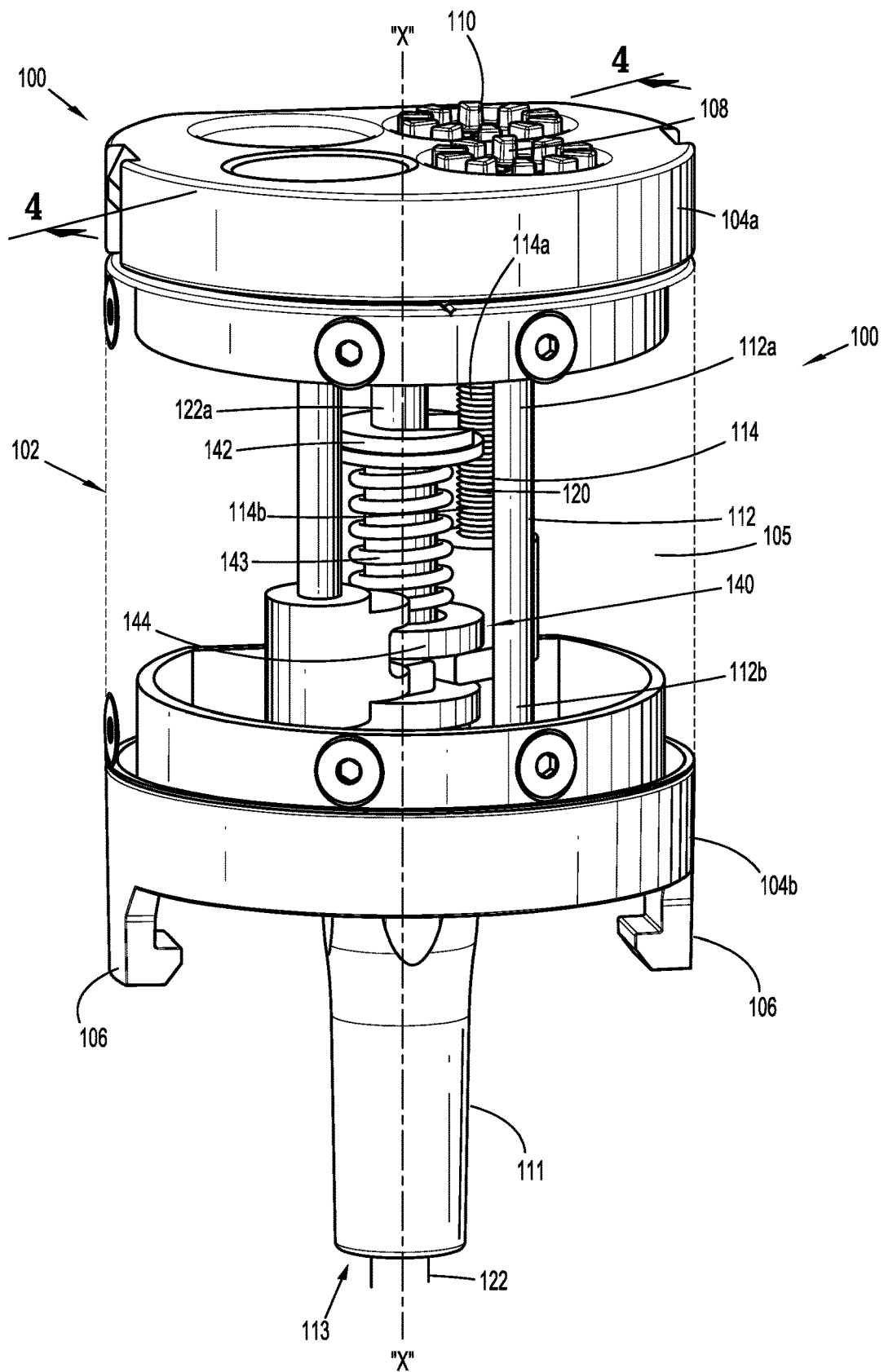
FIG. 3A is an enlarged, side view of an actuation mechanism of the electrosurgical instrument shown in FIG. 2.
Figure 3B:
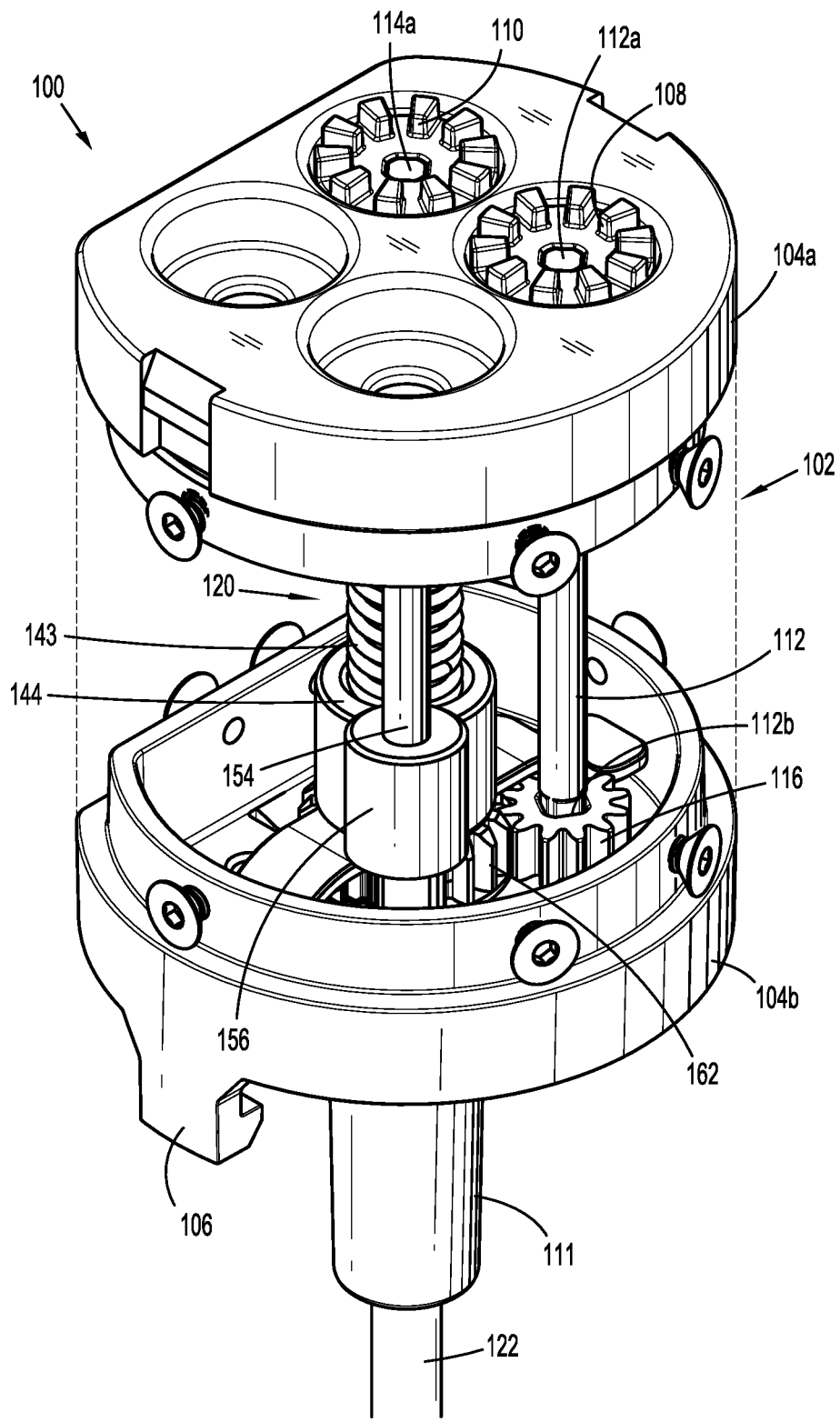
FIG. 3B is a top, perspective view of the actuation mechanism shown in FIG. 3A.

With reference to FIGS. 3A and 3B, as mentioned above, electrosurgical instrument 10 generally includes an actuation mechanism 100 configured to be engaged with instrument drive unit 20 (FIG. 2) and an electrosurgical end effector 200 (FIGS. 8A and 8B), which extends distally from actuation mechanism 100. Actuation mechanism 100 includes a housing 102 and a shaft assembly 120 extending distally from within housing 102. Housing 102 has a generally cylindrical configuration and includes a proximal end 104a and a distal end 104b defining a longitudinal axis "X" therebetween. In embodiments, housing 102 may be any shape suitable for receipt in a distal end 2a (FIG. 2) of robotic arm 2. Proximal and distal ends 104a, 104b of housing 102 are spaced from one another along longitudinal axis "X" to define a cavity 105 therebetween that houses various components of actuation mechanism 100.

Distal end 104b of housing 102 includes a cylindrical projection 111 that extends distally therefrom. Cylindrical projection 111 defines an elongate passageway 113 therethrough. Distal end 104b of housing 102 has a pair of securement members, such as, for example, a pair of resilient or non-resilient fingers 106, extending distally therefrom. Fingers 106 are configured to hook or latch onto a surface of robotic arm 2, e.g., distal end 2a of robotic arm 2, to secure or retain electrosurgical instrument 10 with robotic arm 2. In embodiments, housing 102 may be attached to surgical robotic arm 2 via various fastening engagements, such as, for example, clips, latches, friction fit engagement, buttons, a variety of fasteners, and/or a bayonet-type connection.

With continued reference to FIGS. 3A and 3B, proximal end 104a of housing 102 supports a first input drive coupler 108 configured to be detachably, non-rotatably coupled to one respective drive member (not shown) of instrument drive unit 20, and supports a second input drive coupler 110 configured to be detachably, non-rotatably coupled to another respective drive member (not shown) of instrument drive unit 20. Housing 102 includes a first drive member 112 and a second drive member 114 (FIG. 3A), each being disposed within cavity 105 of housing 102 and extending between proximal end 104a and distal end 104b of housing 102 to fix or locate proximal and distal ends 104a, 104b of housing 102 relative to one another. In some embodiments, housing 102 may include more than two drive members.

Figure 8A:
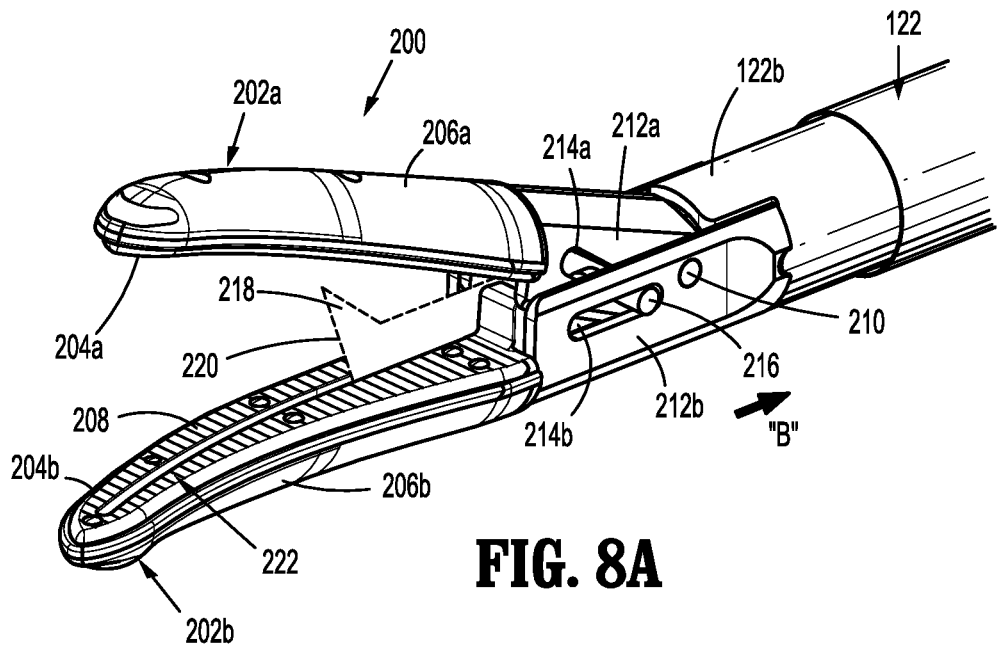
FIG. 8A is a perspective view of an electrosurgical end effector of the electrosurgical instrument of FIG. 2 illustrating jaw members thereof in an expanded configuration.
Figure 8B:
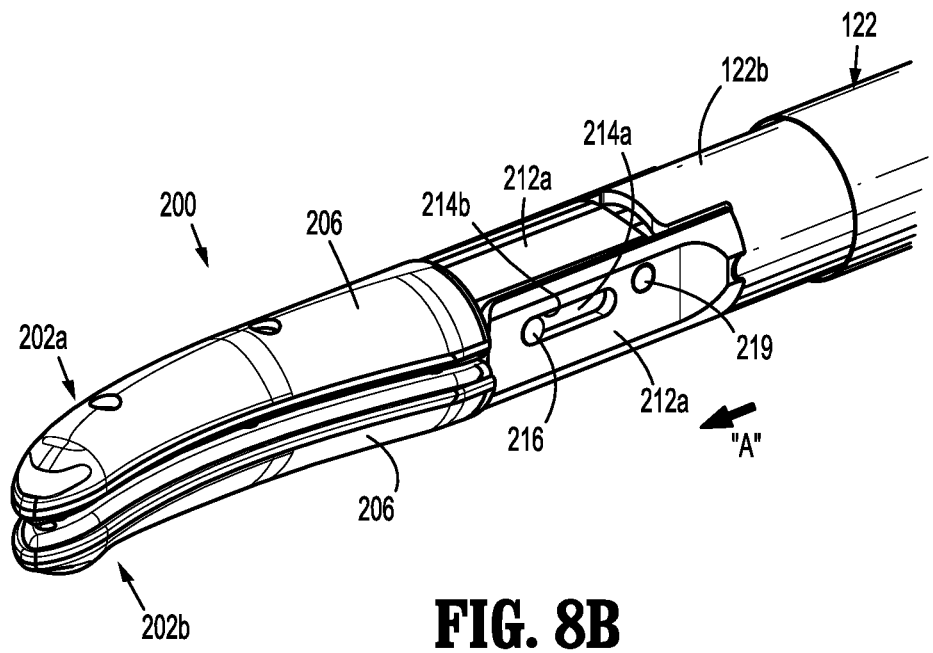
FIG. 8B is a perspective view of the electrosurgical end effector of FIG. 8A illustrating the jaw members thereof in an approximated configuration.

A proximal end 112a of first drive member 112 is non-rotatably coupled to first input drive coupler 108, and a distal end 112b of first drive member 112 is operatively coupled to knife blade 218 (FIG. 8A) of electrosurgical end effector 200. A proximal end 114a of second drive member 114 is non-rotatably coupled to second input drive coupler 110 and a distal end 114b of second drive member 114 is operatively coupled to one or both of jaw members 202a, 202b of electrosurgical end effector 200 (FIGS. 8A and 8B). As such, upon actuation of motors (not shown) of instrument drive unit 20, the drive members (not shown) of instrument drive unit 20 rotate, resulting in concomitant rotation of first and second drive members 112, 114 of actuation mechanism 100 via the first and second input drive couplers 108, 110 of housing 102. The rotation of first drive member 112 of actuation mechanism 100 ultimately results in the actuation of knife blade 218 (FIG. 8A) of electrosurgical instrument 200, and the rotation of second drive member 114 of actuation mechanism 100 ultimately results in the actuation of jaw members 202a, 202b (FIGS. 8A and 8B) of electrosurgical end effector 200, as described in greater detail below.

With reference to FIGS. 3A, 3B, 4, and 5, the components of actuation mechanism 100 responsible for actuating jaw members 202a, 202b of electrosurgical end effector 200 will now be described. As briefly mentioned above, actuation mechanism 100 includes shaft assembly 120. Shaft assembly 120 extends distally from housing 102, is at least partially disposed within cavity 105 of housing 102, and operatively intercouples instrument drive unit 20 with knife blade 218 (FIG. 8A) and jaw members 202a, 202b (FIGS. 8A and 8B) of electrosurgical end effector 200.

Figure 4:
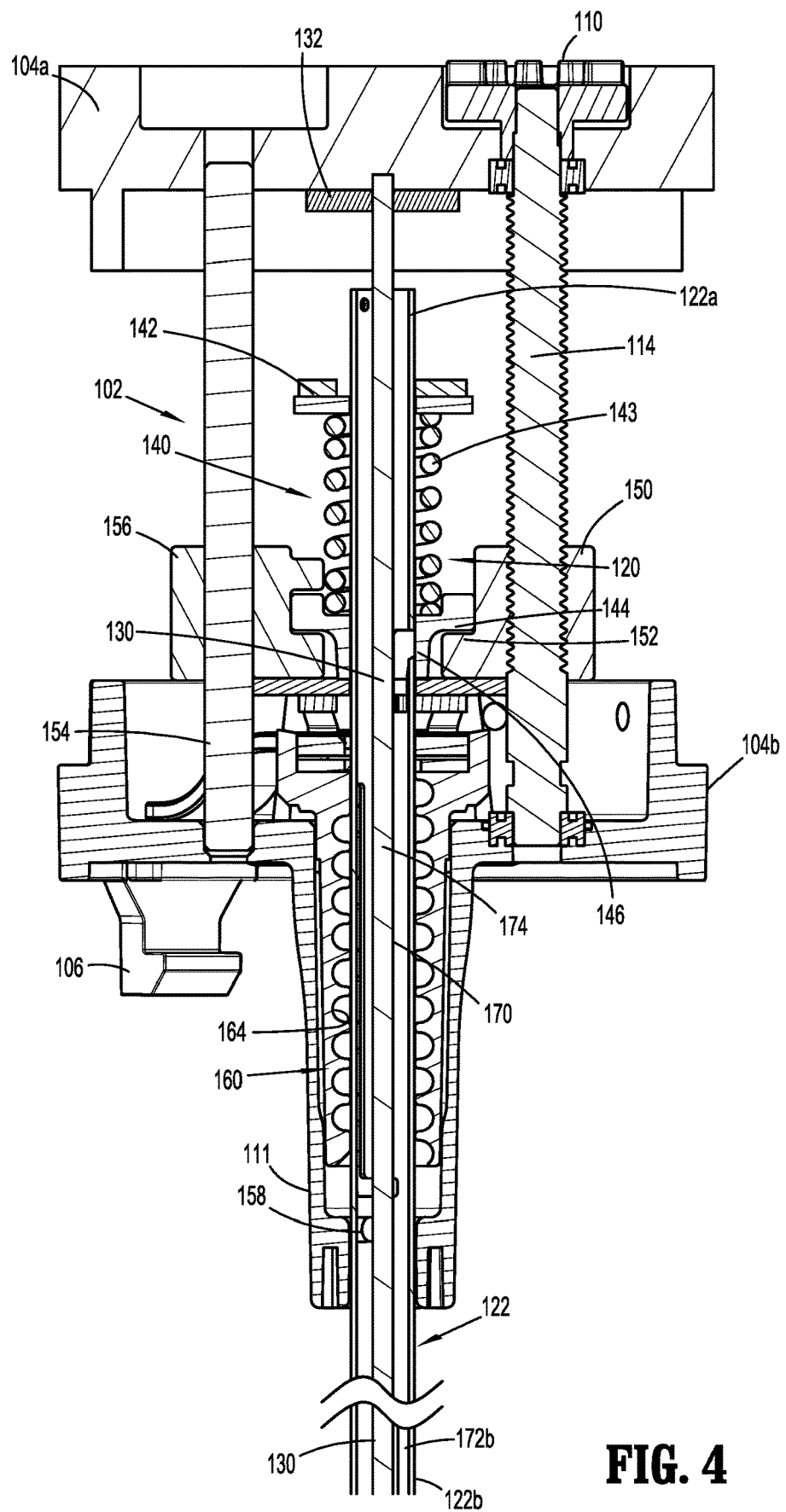
FIG. 4 is a cross-section, taken along line 4-4 in FIG. 3A, of the actuation mechanism.
Figure 5:
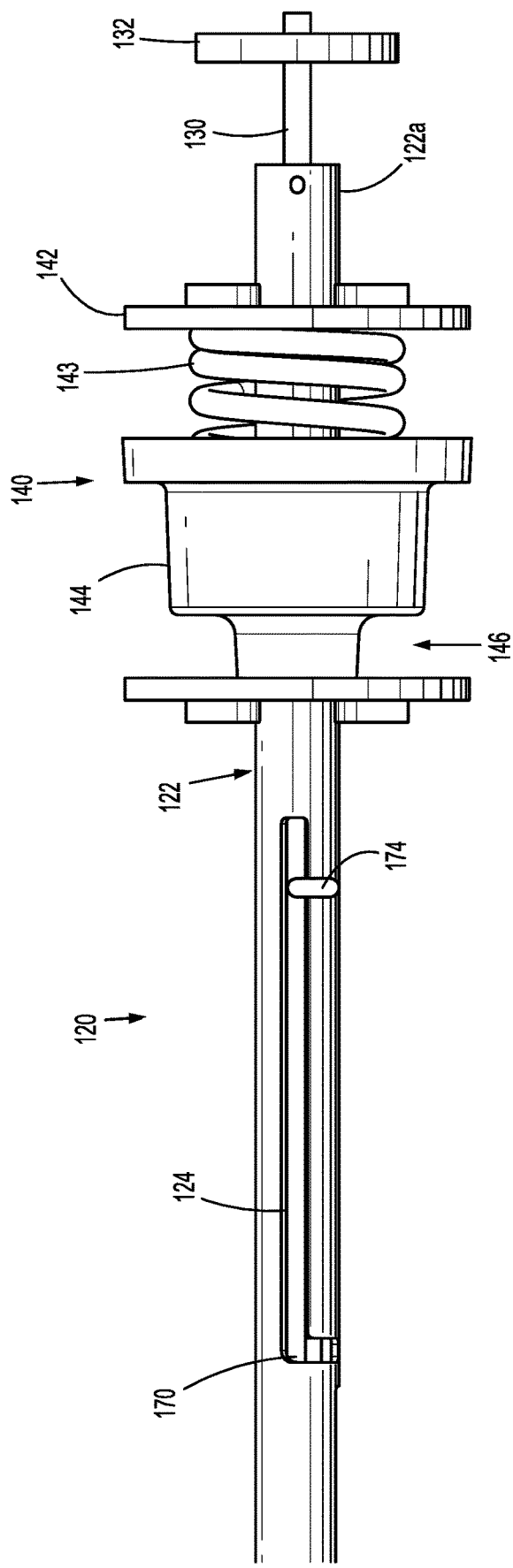
FIG. 5 is a side view of a shaft assembly, with parts removed, of the actuation mechanism of FIG. 4.

With specific reference to FIGS. 4 and 5, shaft assembly 120 includes a shaft 122, a rod 130 extending therethrough, and a collar assembly 140 fixedly disposed about a proximal end 122a of shaft 122. Shaft 122 has a proximal end 122a, and a distal end 122b (FIGS. 8A and 8B), which is mechanically attached to one or both jaw members 202a, 202b of electrosurgical end effector 200. With distal end 122b of shaft 122 mechanically attached to one or both jaw members 202a, 202b, proximal or distal longitudinal movement of shaft 122 results in corresponding proximal or distal longitudinal movement of jaw members 202a, 202b. In embodiments, housing 102 may further include a set screw 158 (FIG. 4) engaged to shaft 122 to prevent shaft 122 from rotating within housing 102.

Rod 130 of shaft assembly 120 extends from proximal end 104a of housing 102, through the length of shaft 122, and terminates at jaw members 202a, 202b of electrosurgical end effector 200. Rod 130 has a proximally disposed annular member 132 fixed with proximal end 104a of housing 102, such that rod 130 is prevented from longitudinal movement relative to housing 102. As such, shaft 122 can translate longitudinally along and relative to rod 130 to open or close jaw members 202a, 202b of electrosurgical end effector 200.

With continued reference to FIGS. 4 and 5, collar assembly 140 of shaft assembly 120 includes a proximal collar 142, a distal collar 144, and a biasing member 143 interconnecting proximal and distal collars 142, 144. Proximal collar 142 is fixed to proximal end 122a of shaft 122 such that relative translation of proximal collar 142 and shaft 122 is prohibited. Distal collar 144 is slidably engaged to shaft 122 and coupled to proximal collar 142 via biasing member 143, which may be in the form of a coil or compression spring. In some embodiments, distal collar 144 may be fixedly engaged to shaft 122 such that longitudinal movement of distal collar 144 results in corresponding longitudinal motion of shaft 122.

Biasing member 143 provides a dampening effect to proximal and/or distal motion of collar assembly 140 (i.e., there is a delay between when distal collar 144 is moved relative to shaft 122 and when relative movement between proximal collar 142 and distal collar 144 ceases). Biasing member 143 functions as overload protection such that the jaw members 202a, 202b do not clamp too hard on tissue that is disposed between the jaw members 202a, 202b. The jaw members 202a, 202b are opened and closed by moving the shaft assembly 120 a set distance, with no regard for the force required to render said movement. If there is tissue between the jaw members 202a, 202b, the jaw members 202a, 202b cannot completely close. As such, if the robotic surgical system 1 was actuated to move the shaft assembly 120 (to close the jaw members 202a, 202b) by the preset distance, the force applied would be equal to the highest force the motors (1 . . . n) could output. When the jaw members 202a, 202b try to close on tissue, the force applied to the shaft assembly 120 is equal to the spring force of the biasing member 143, as defined by the relation $F=k_x+b$, where b is the preload force (spring force at rest), and $k_x$ is the spring constant multiplied by the distance the robotic surgical system 1 tries to move the shaft assembly 120, after the jaw members 202a, 202b have been blocked by tissue.

Figure 6:
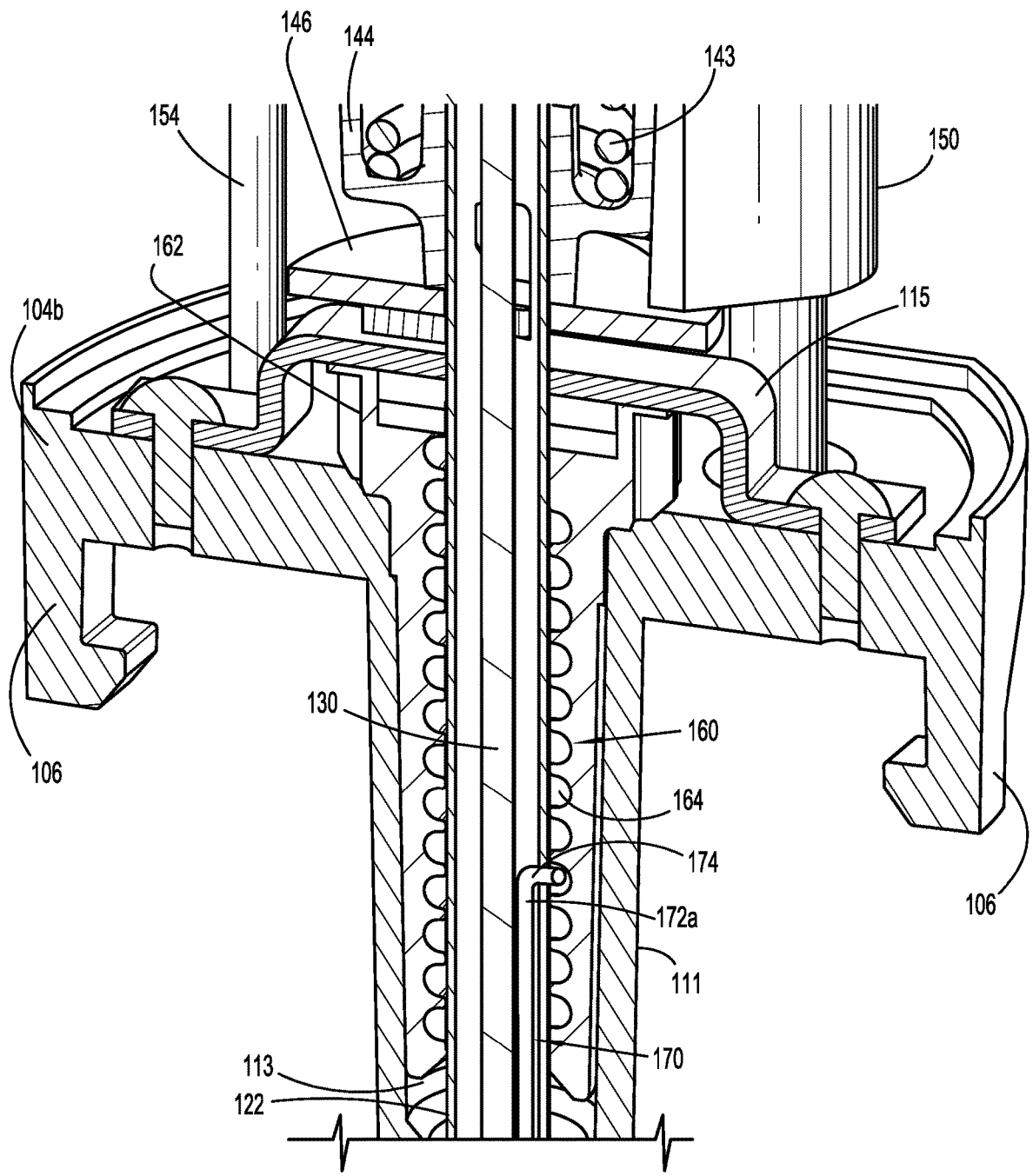
FIG. 6 is an enlarged, perspective view of the cross-section shown in FIG. 4.

With reference to FIGS. 3A, 4, and 6, distal collar 144 defines an annular cavity 146 for receipt therein of a protrusion 152 of a shroud, such as, for example, a nut 150 that is in threaded engagement with second drive member 114. Shroud 150 is threadedly engaged to second drive member 114 such that rotation of second drive member 114 results in longitudinal movement of shroud 150 along second drive member 114. Shroud 150 has a protrusion 152 extending laterally therefrom and is received in annular cavity 146 of distal collar 144 such that proximal and distal movement of shroud 150, via rotation of second drive member 114, results in corresponding proximal and distal movement of distal collar 114. Protrusion 152 of shroud 150 may have a c-shaped configuration to capture or at least partially surround distal collar 144 therein, thus preventing or inhibiting shroud 150 from rotating relative to second drive member 114 during rotation of second drive member 114. Therefore, movement of shroud 150 relative to second drive member 114 is limited to longitudinal movement along second drive member 114.

In embodiments, a plurality of threaded drive members, similar to second drive member 114, with associated shrouds, similar to shroud 150, may be provided. The plurality of threaded drive members may be used to reduce offset loading on each threaded drive member and to reduce a load carried by each shroud threadedly engaged thereto. The shrouds, e.g., nuts, may be calibrated to be on the same horizontal level as one another, and to move synchronously with one another to distally or proximally longitudinally move the associated collar assembly 140.

In some embodiments, housing 102 may further include one or more guideposts 154 (FIG. 4) extending between proximal and distal ends 104, 104b of housing 102. Another shroud 156 may be slidably disposed about each guidepost 154, and may capture distal collar 144 of collar assembly 140 therein to help guide distal collar 144 along longitudinal axis "X."

In use, the second drive member (not shown) of instrument drive unit 20 drives rotation of second drive member 114 of actuation mechanism 100 via second input drive coupler 110. Rotation of second drive member 114 drives either proximal or distal longitudinal movement of shroud 150 along second drive member 114. Proximal or distal longitudinal movement of shroud 150 relative to second drive member 114 drives the concomitant proximal or distal longitudinal movement of distal collar 144 of collar assembly 140, relative to shaft 122 and proximal collar 142, via the abutting engagement of protrusion 152 of shroud 150 within annular cavity 146 of distal collar 144.

Proximal or distal longitudinal movement of distal collar 144 relative to shaft 122 and proximal collar 142 ceases after biasing member 143 achieves a threshold compression (via proximal longitudinal movement) or a threshold extension (via distal longitudinal movement). Upon biasing member 143 achieving the threshold compression or extension, the continued proximal or distal longitudinal movement of distal collar 144 causes corresponding proximal or distal longitudinal movement of proximal collar 142 of collar assembly 144 via the interconnection of proximal and distal collars 142, 144 provided by biasing member 143. Proximal or distal longitudinal movement of proximal collar 142 results in corresponding proximal or distal longitudinal movement of shaft 122 due to proximal collar 142 being fixedly engaged with shaft 122.

As such, rotation of second drive member 114 axially moves shaft 122 relative to housing 102. Axial movement of shaft 122 relative to housing 102 actuates jaw members 202a, 202b of electrosurgical instrument 200, as will be described in detail below with reference to FIGS. 8A and 8B.

With reference to FIGS. 4-7, the components of actuation mechanism 100 responsible for actuating knife blade 218 (FIG. 8A) of electrosurgical end effector 200 will now be described. Shaft assembly 120 further includes a cannulated, elongate collar 160 and a longitudinally extending actuation bar 170 in operative communication with elongate collar 160. Elongate collar 160 is rotatably disposed within elongated passageway 113 defined through cylindrical projection 111 of distal end 104b of housing 102. Elongate collar 160 is prevented from moving axially relative to housing 102 by a capture member or bracket 115 (FIG. 6). Shaft 122 of shaft assembly 120 extends coaxially through elongate collar 160, reducing the overall size of electrosurgical instrument 10. Elongate collar 160 is rotatable around shaft 122, and shaft 122 is longitudinally movable within and relative to elongate collar 160 such that independent actuation of jaw members 202a, 202b (FIGS. 8A and 8B) and knife blade 218 (FIG. 8A) of electrosurgical end effector 200 is provided.

Figure 7:
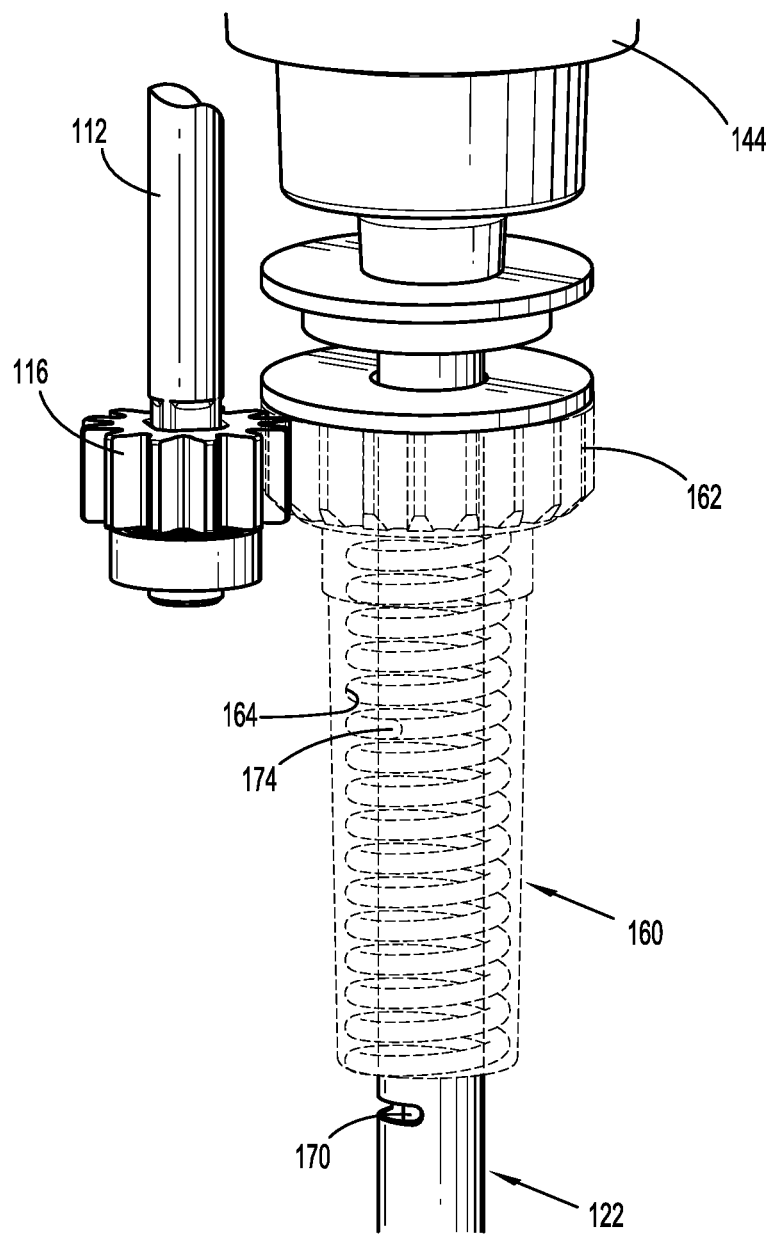
FIG. 7 is a perspective view, in part phantom, of components of the shaft assembly of the actuation mechanism of FIGS. 3A and 3B.

With reference to FIGS. 6 and 7, a proximal end of elongate collar 160 has a gear, for example, a spur gear 162, and distal end 112b of first drive member 112 includes a gear, such as, for example, a spur gear 116 (FIG. 3B). Spur gear 162 of elongate collar 160 and spur gear 116 (FIG. 3B) of first drive member 112 are in meshing engagement with one another such that rotation of first drive member 112 rotates elongate collar 160 relative to housing 102. Spur gear 162 of elongate collar 160 has a larger circumference than passageway 113 of housing 102 in which elongate collar 160 is rotatably received so that elongate collar 160 is prevented from moving distally through passageway 113, relative to housing 102. Elongate collar 160 is prevented from moving proximally relative to housing 102 due to capture member or bracket 115 covering spur gear 162 of elongate collar 160. In embodiments, gears 116, 162 may be in the form of various types of gears, such as, for example, helical gears, miter gears, worm gears, anti-backlash gears, bevel gears, cluster gears, differential end gears, composite spur gears, and other gears known in the art.

Elongate collar 160 has an internal threadform 164 extending along a length thereof. Internal threadform 164 is sized to interface with an extension 174 of longitudinal bar 170, as described herein. In embodiments, elongate collar 160 may be monolithically formed. Internal threadform 164 may have one thread or two threads. In one embodiment, elongate collar 160 includes a first longitudinal half and a second longitudinal half adhered or mechanically located with respect to one another (e.g., keying features may locate the two halves with respect to one another while the passageway 113 elongate collar 160 rotates in would keep the two halves held together). Each longitudinal half contains a set of two threads, starting at a rotational angle of 180° relative to one another, to provide for a single, continuous threadform along which extension 174 of longitudinal bar 170 can traverse.

With continued reference to FIGS. 4-7, longitudinal bar 170 of shaft assembly 120 has a proximal end 172a and a distal end 172b (FIG. 4). Proximal end 172a of longitudinal bar 170 is disposed within shaft 122 of shaft assembly 120 and is in engagement with internal threadform 164 of elongate collar 160. Distal end 172b of longitudinal bar 170 is coupled to knife blade 218 (FIG. 8A). Proximal end 172a of longitudinal bar 170 includes an extension 174 angled in substantially perpendicular relation to the remainder of longitudinal bar 170. Extension 174 has an arcuate configuration and is dimensioned to extend into a depth of internal threadform 164 of elongate collar 160 and ride therealong as elongate collar 160 rotates. It is contemplated that the extension 174 of the longitudinal bar 170 extends in a clockwise direction from proximal end 172a of longitudinal bar 170.

Shaft 122 includes a longitudinal slot 124 (FIG. 5) formed therein having a length substantially equal to a length of internal threadform 164 of elongate collar 160. Extension 174 of longitudinal bar 170 protrudes from within shaft 122 and through longitudinal slot 124 of shaft 122 into internal threadform 164 of elongate collar 160. Extension 174 of longitudinal bar 170 is slidably retained within longitudinal slot 124 of shaft 122 to prevent longitudinal bar 170 from rotating relative to shaft 122. As such, movement of extension 174 is limited to longitudinal movement along longitudinal slot 124 relative to shaft 122.

In operation, the first drive member (not shown) of instrument drive unit 20 (FIG. 2) is actuated to rotate first drive member 112 of actuation mechanism 100 via first input drive coupler 108. Rotation of first drive shaft 112 rotates elongate collar 160 within and relative to shaft 122 via the meshing engagement of spur gears 116, 162 of first drive member 112 and elongate collar 160, respectively. As elongate collar 160 rotates within and relative to shaft 122, extension 174 of longitudinal bar 170 rides along helical threads of internal threadform 164 to drive either proximal or distal movement of longitudinal bar 170 relative to elongate collar 160 and shaft 122.

Since knife blade 218 (FIG. 8A) is coupled to distal end 172b of longitudinal bar 170, proximal or distal longitudinal movement of longitudinal bar 170 moves knife blade 218 (FIG. 8A) in a corresponding motion. It is contemplated that clockwise rotation of elongate collar 160 drives a distal movement of knife blade 218 and that a counter-clockwise rotation of elongate collar 160 drives a proximal movement of knife blade 218.

With reference to FIGS. 8A and 8B, the components of electrosurgical end effector 200 will now be described. Electrosurgical end effector 200 is operatively coupled to actuation mechanism 100 and extends distally therefrom. Electrosurgical end effector 200 generally includes a pair of opposing jaw members 202a, 202b. Electrosurgical end effector 200 may be moved, by actuation mechanism 100, from the open configuration (FIG. 8A) wherein tissue (not shown) is received between jaw members 202a, 202b, and a closed configuration (FIG. 8B), wherein the tissue is clamped and treated. Jaw members 202a, 202b pivot about a pivot pin 210 to move electrosurgical end effector 200 to the closed configuration, wherein sealing plates 204a, 204b provide a pressure to tissue grasped therebetween, as described below. In some embodiments, to provide an effective tissue seal, a pressure within a range between about 3 kg/cm to about 16 kg/cm and, desirably, within a working range of about 7 kg/cm to about 13 kg/cm, may be applied to the tissue.

The upper and lower jaw members 202a, 202b are electrically coupled to a cable (not shown), and to a generator (not shown), via respective suitable electrical wiring extending through shaft 122 of actuation mechanism 100 to provide an electrical pathway to a pair of electrically conductive, tissue-engaging sealing plates 204a, 204b disposed on the upper and lower jaw members 202a, 202b, respectively. The sealing plate 204a of upper jaw member 202a opposes the sealing plate 204b of lower jaw member 202b. In some embodiments, the sealing plates 204a, 204b are electrically coupled to opposite terminals, e.g., positive or active (+) and negative or return (−) terminals associated with the generator. Thus, bipolar energy may be provided through the sealing plates 204a, 204b to tissue. Alternatively, the sealing plates 204a, 204b may be configured to deliver monopolar energy to tissue. In a monopolar configuration, one or both sealing plates 204a, 204b deliver electrosurgical energy from an active terminal, e.g., (+), while a return pad (not shown) is placed generally on a patient and provides a return path to the opposite terminal, e.g., (−), of the generator. Each jaw member 202a, 202b includes a jaw insert (not shown) and an insulator 206a, 206b that serves to electrically insulate the sealing plates 204a, 204b from the jaw insert of the jaw members 202a, 202b, respectively.

In the closed configuration, a separation or gap distance is maintained between the sealing plates 204a, 204b by an array of stop members 208 (FIG. 8A) disposed on or adjacent the sealing plates 204a, 204b. The stop members 208 contact opposing surfaces on the opposing jaw members 202a, 202b and prohibit further approximation of the sealing plates 204a, 204b. In some embodiments, to provide an effective tissue seal, an appropriate gap distance of about 0.001 inches to about 0.010 inches and, desirably, between about 0.002 inches to about 0.005 inches, may be provided. In some embodiments, the stop members 208 are constructed of a heat-resistant ceramic deposited onto the jaw members 202a, 202b. In other embodiments, the stop members 208 are constructed of an electrically non-conductive plastic molded onto the jaw members 202a, 202b, e.g., by a process such as overmolding or injection molding.

A pivot pin 210 extends through a proximal portion 212a, 212b of each of the jaw members 202a, 202b to pivotally support the jaw members 202a, 202b. Pivot pin 210 permits jaw members 202a, 202b to pivot thereabout to move electrosurgical end effector 200 between the open and closed configurations (FIGS. 8A and 8B, respectively). Pivot pin 210 limits relative movement of the jaw members 202a, 202b to pivoting movement.

Proximal portion 212a, 212b of each of the jaw members 202a, 202b also includes a lateral cam slot 214a, 214b extending therethrough. Lateral cam slot 214a of upper jaw member 202a extends in oblique relation to a longitudinal axis defined by upper jaw member 202a. Lateral cam slot 214b of lower jaw member 202b extends in parallel relation to a longitudinal axis defined by lower jaw member 202b. In this way, lateral cam slot 214a of upper jaw member 202a is angled relative to lateral cam slot 214b of lower jaw member 202b when the jaw members 202a, 202b are disposed in the closed configuration. A cam pin 216 extends through lateral cam slots 214a, 214b of jaw members 202a, 202b and is longitudinally movable through lateral cam slots 214a, 214b. Cam pin 116 is mechanically coupled (e.g., via welding, friction-fit, laser welding, etc.) to a distal end of rod 130 (FIG. 4) of shaft assembly 120. As mentioned above, rod 130 is prevented from longitudinal movement relative to housing 102 of actuation mechanism 100 due to the fixed engagement of annular member 132 of rod 130 with housing 102 of actuation mechanism 100. Therefore, cam pin 116, via its mechanical coupling to rod 130, is also prevented from longitudinal movement relative to housing 102 of actuation mechanism 100.

In operation, to open jaw members 202a, 202b to the expanded configuration shown in FIG. 8A, shaft 122 of shaft assembly 120 is translated in a distal direction indicated by arrow "A" shown in FIG. 8B, via actuation by actuation mechanism 100 in the manner described above. As mentioned above, distal end 122b of shaft 122 is mechanically coupled to jaw members 202a, 202b. As such, distal longitudinal movement of shaft 122 results in corresponding distal longitudinal movement of jaw members 202a, 202b along rod 130 relative to housing 102 and cam pin 216. As jaw members 202a, 202b translate distally relative to housing 102 and cam pin 216, the interaction between lateral cam slots 214a, 214b of upper and lower jaw members 202a, 202b and cam pin 216 forces upper jaw member 202a apart from lower jaw member 202b.

To close jaw members 202a, 202b to the approximated configuration shown in FIG. 8B, shaft 122 is translated in a proximal direction indicated by arrow "B" in FIG. 8A, via actuation by actuation mechanism 100 in the manner described above. As shaft 122 translates proximally along rod 130 relative to housing 102 and cam pin 216, the interaction between lateral cam slots 214a, 214b of upper and lower jaw members 202a, 202b and cam pin 216 draws upper jaw member 202a closer to lower jaw member 202b.

Upon approximating jaw members 202a, 202b, electrosurgical energy may be delivered, by an electrosurgical generator (not shown), to the tissue through the electrically conductive seal plates 204a, 204b to effect a tissue seal. Once a tissue seal is established, the sealed tissue or portion thereof may be severed by knife blade 218. To sever the sealed tissue, longitudinal bar 170 (FIGS. 4-7) is translated distally relative to housing 102 via actuation of actuation mechanism 100 in the manner described above. As mentioned above, longitudinal bar 170 (FIGS. 4-7) of actuation mechanism 100 is coupled at a distal-most end to knife blade 218. Therefore, as longitudinal bar 170 translates distally, knife blade 218, having a sharpened distal edge 220, will also move distally through a knife channel 222 defined in one or both jaw members 202a, 202b to transect the sealed tissue.

In some embodiments, robotic surgical system 1 may further include a virtual foot switch (not shown) in electrical communication with an electrosurgical generator. A relay circuit may be implemented into operating console 5 to allow robotic surgical system 1 to open and close the virtual foot-switch circuit. As the circuit is opened and closed, the electrosurgical generator would receive a signal that an OEM foot switch was depressed and released, causing the electrosurgical generator to deliver electrosurgical energy to electrosurgical end effector 200.

With reference to FIGS. 9-12, another embodiment of a surgical instrument, such as, for example, an electrosurgical instrument 300, is provided, similar to electrosurgical instrument 10 described above. Electrosurgical instrument 300 is configured to be attached to robotic arm 2 (FIG. 2) and to be a component of surgical robotic system 1. Electrosurgical instrument 300 includes an actuation mechanism 302, similar to actuation mechanism 100 described above, and an electrosurgical end effector 304, similar to electrosurgical end effector 200 described above. Actuation mechanism 302 of electrosurgical instrument 300 interfaces with one of the surgical robotic arms 2, 3 (FIG. 2) and is operatively engaged to electrosurgical end effector 304 to actuate functions of electrosurgical end effector 304 via power delivered by the instrument drive unit 20 (FIG. 2).

Figure 9:
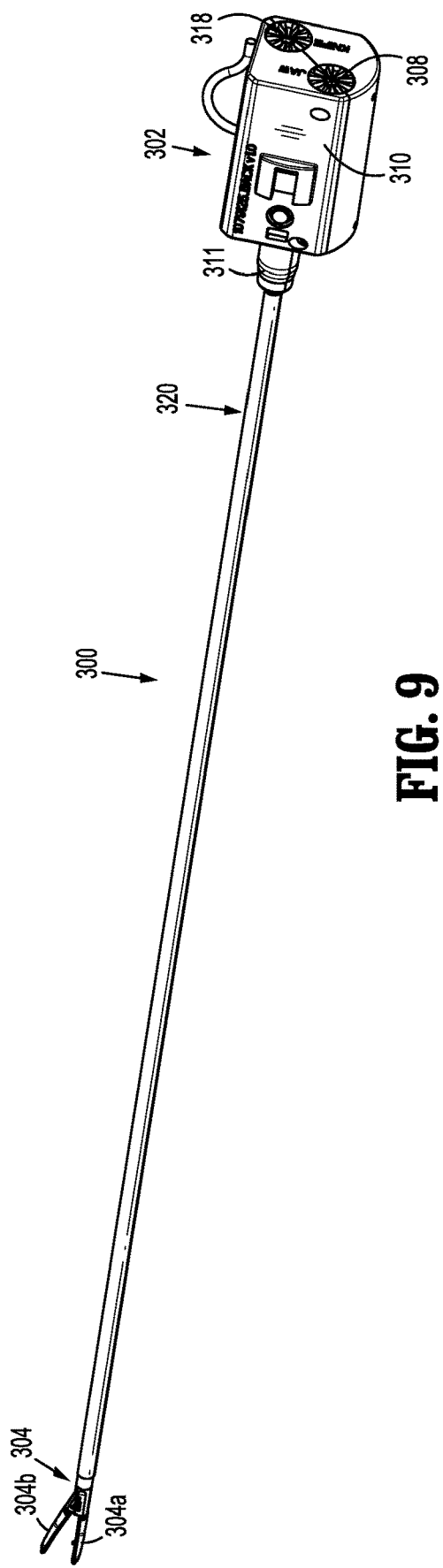
FIG. 9 is a perspective view of an electrosurgical instrument in accordance with another embodiment of the present disclosure.
Figure 10:
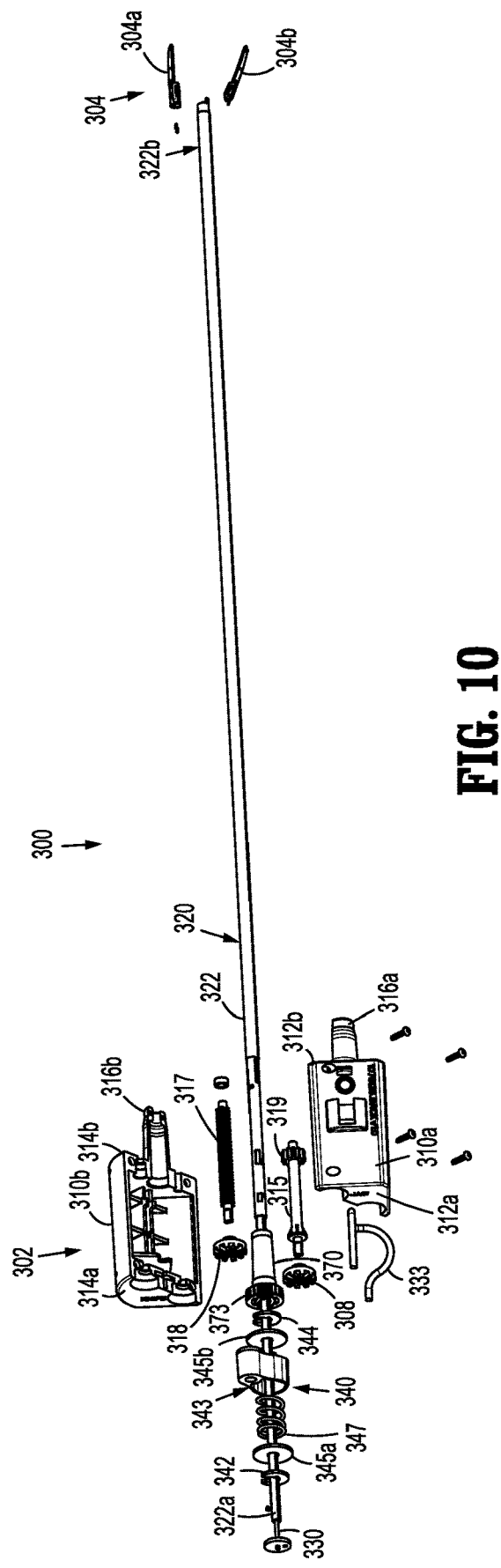
FIG. 10 is a perspective view, with parts separated, of the electrosurgical instrument of FIG. 9.
Figure 11:
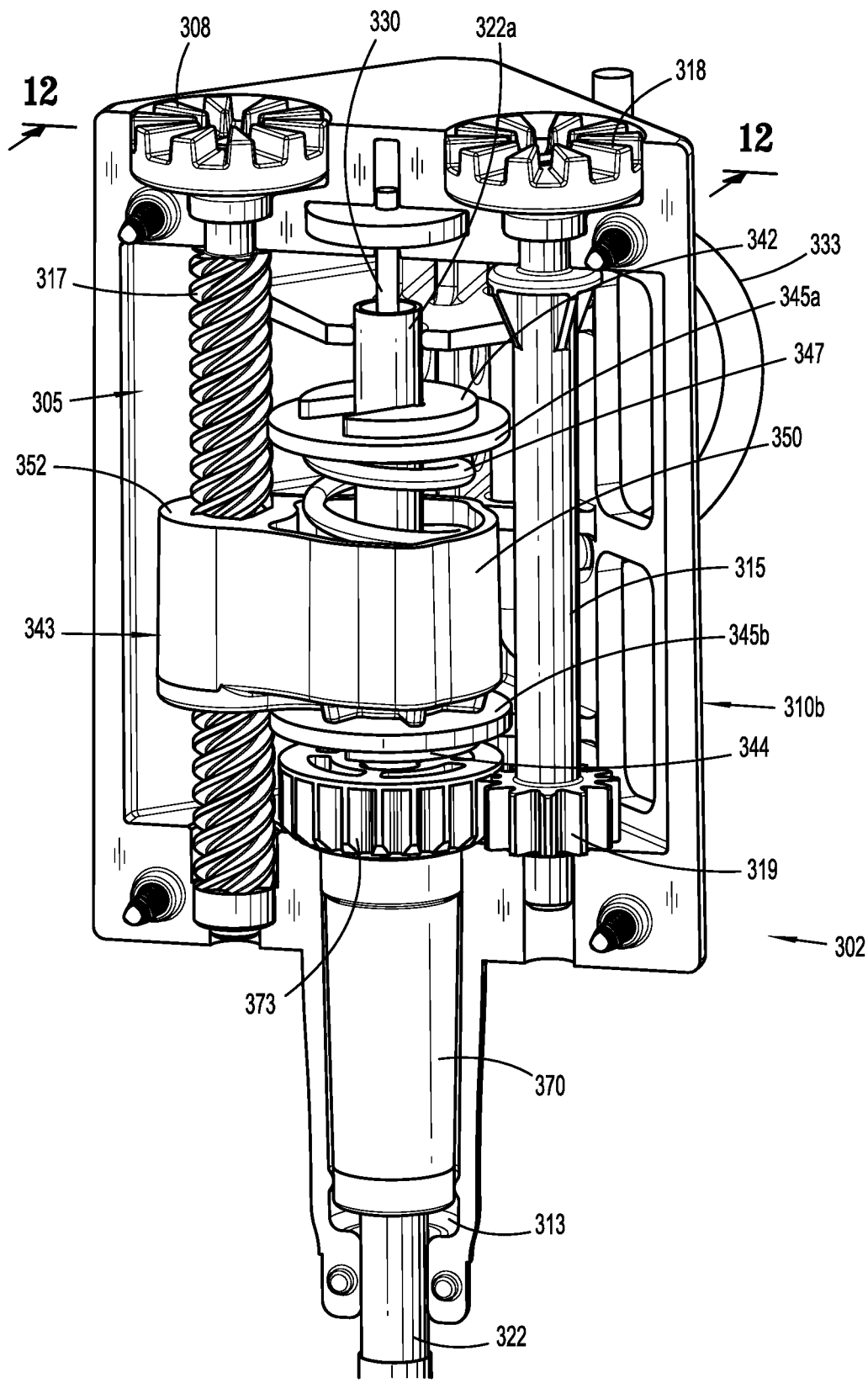
FIG. 11 is an enlarged, cutaway view of an actuation mechanism of the electrosurgical instrument of FIG. 9.

With reference to FIGS. 9-11, actuation mechanism 302 includes a housing 310 and a shaft assembly 320 extending distally from within housing 310. Housing 310 has a generally rectangular or D-shaped transverse cross-sectional profile. Unlike housing 102 of electrosurgical instrument 100 described above, housing 310 of electrosurgical instrument 300 includes two complimentary longitudinal sections, such as, for example, housing halves 310a, 310b that are detachably connected to one another using fasteners. In some embodiments, housing halves 310a, 310b may be configured to be detachably connected to one another via a snap fit engagement. Each housing half 310a, 310b includes a proximal end 312a, 314a and a distal end 312b, 314b. Upon assembling housing halves 310a, 310b to one another, proximal ends 312a, 314a of housing halves 310a, 310b are adjacent one another and distal ends 312b, 314b of housing halves 310a, 310b are adjacent one another. When assembled, housing halves 310a, 310b together define a cavity 305 that houses and retains various components of actuation mechanism 302. Distal ends 312b, 314b of housing halves 310a, 310b each have a hemi-spherical extension 316a, 316b extending distally therefrom. Upon assembling housing halves 310a, 310b to one another, hemi-spherical extensions 316a, 316b form a cylindrical projection or stem 311 that defines an elongate passageway 313 therethrough.

Proximal ends 312a, 314a of housing 310 support a first input drive coupler 308 configured to be detachably, non-rotatably coupled to one respective drive member (not shown) of instrument drive unit 20. Proximal ends 312a, 314a of housing 310 also support a second input drive coupler 318 configured to be detachably, non-rotatably coupled to another respective drive member (not shown) of instrument drive unit 20. Housing 310 includes a first drive member 315 and a second drive member 317, each being rotatably disposed within cavity 305 of housing 310. First drive member 315 is non-rotatably connected to first input drive coupler 308 and second drive member 317 is non-rotatably connected to second input drive coupler 318. First drive member 315 has a distally located gear in meshing engagement with a gear 373 of an elongated collar 370.

Housing 310 further includes a wire 333 connected to housing half 310b and extending within cavity 305 of housing 310. Wire 333 is configured to be connected to and powered by an electrosurgical generator (not shown). Wire 333 is electrically coupled to jaw members 304a, 304b of end effector 304 (FIG. 9), via shaft 322, to provide electrosurgical energy to end effector 304.

Figure 12:
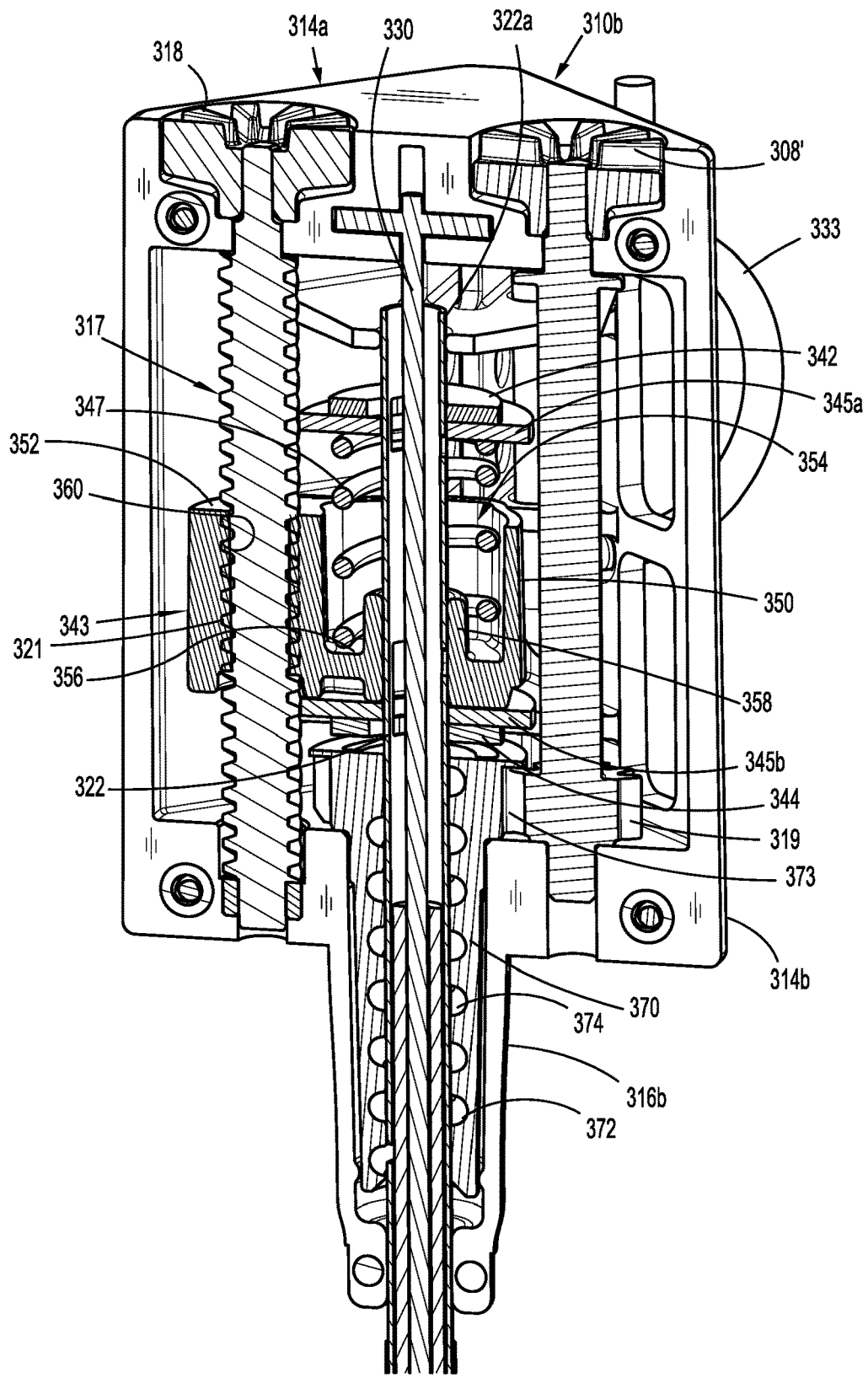
FIG. 12 is a cross-sectional view, taken along section lines 12-12 of FIG. 11, of the actuation mechanism.

With reference to FIGS. 10-12, actuation mechanism 302 includes a shaft assembly 320, similar to shaft assembly 120 described above. Shaft assembly 320 includes a shaft 322, a rod 330 extending through shaft 322, and a collar assembly 340 disposed about a proximal end 322a of shaft 322. Shaft 322 has a proximal end 322a, and a distal end 322b, which is mechanically attached to one or both jaw members 304a, 304b of electrosurgical end effector 304. With distal end 322b of shaft 322 mechanically attached to one or both jaw members 304a, 304b, proximal or distal longitudinal movement of shaft 322 effects an opening or closing of jaw members 304a, 304b, in a similar manner as described above with regard to FIGS. 1-8B.

Collar assembly 340 of shaft assembly 320 includes a proximal collar 342, a distal collar 344, and an intermediate collar 343 disposed between first and second collars 342, 344. Proximal and distal collars 342, 344 are spaced from one another along shaft 322 and are fixed to proximal end 322a of shaft 322 such that relative translation of proximal and distal collars 342, 344 and shaft 322 is prohibited. Proximal and distal washers 345a, 345b are disposed along shaft 322 and configured for engagement with proximal and distal collars 342, 344, respectively.

With reference to FIGS. 11 and 12, intermediate collar 343 is slidably engaged to shaft 322 and operatively coupled to proximal collar 342 via a biasing member 347, which may be in the form of a coil or compression spring. Unlike actuation mechanism 100 described above, actuation mechanism 302 does not include a shroud 150 (FIG. 4) for interconnecting intermediate collar 343 to second drive member 317. Instead, intermediate collar 343 is directly connected to drive member 317. In particular, intermediate collar 343 includes a main body 350 disposed about shaft 322, and an outrigger 352 extending laterally from the main body 350 and disposed about drive member 317, such that intermediate collar 343 interconnects shaft 322 to drive member 317. Main body 350 of intermediate collar 343 has a generally cylindrical configuration and defines a counterbore 354. Counterbore 354 has a flat-bottomed hole 356 configured to house biasing member 347 therein. A cylindrical, cannulated extension 358 projects upwardly from flat-bottomed hole 356. Extension 358 slidably receives shaft 322 therein. Outrigger 352 of intermediate collar 343 includes an internal threadform 360 threadedly engaged to threads 321 of drive member 317 such that intermediate collar 343 moves along drive member 317 in response to rotation of drive member 317. Rotation of intermediate collar 343 within housing 310 is resisted by housing halves 310a, 310b.

In assembly, the components of actuation mechanism 302 are loaded into either first housing half 310a or second housing half 310b. The other of the first and second housing halves 310a, 310b is then engaged to the first housing half 310a or the second housing half 310b to enclose the components within cavity 305 of housing 310.

In use, the second drive member (not shown) of instrument drive unit 20 drives rotation of second drive member 317 of actuation mechanism 302 via second input drive coupler 318. Rotation of second drive member 317 drives either proximal or distal longitudinal movement of intermediate collar 343 along second drive member 317 via the threaded engagement of outrigger 352 of intermediate collar 343 and second drive member 317. Proximal longitudinal movement of intermediate collar 343 relative to second drive member 317 effects proximal longitudinal movement of proximal collar 342 due to the operative engagement of intermediate collar 343 with proximal collar 342 via biasing member 347. Proximal longitudinal movement of proximal collar 342 results in corresponding proximal longitudinal movement of shaft 322 due to proximal collar 342 being fixedly engaged with proximal end 322a of shaft 322.

Distal longitudinal movement of intermediate collar 343 relative to second drive member 317 effects distal longitudinal movement of distal collar 344 via the abutting engagement of intermediate collar 343 with distal collar 344. Distal longitudinal movement of distal collar 344 results in corresponding distal longitudinal movement of shaft 322 due to distal collar 344 being fixedly engaged with proximal end 322a of shaft 322.

As such, rotation of second drive member 317 axially moves shaft 322 relative to housing 310 in proximal or distal directions. Axial movement of shaft 322 relative to housing 310 actuates jaw members 304a, 304b of electrosurgical instrument 304, in a similar manner as described in detail above with reference to FIGS. 8A and 8B.

With reference to FIGS. 11 and 12, similar to actuation mechanism 100 of surgical instrument 10 described above, actuation mechanism 300 of surgical instrument 300 further includes an elongate collar 370 configured to actuate longitudinal movement of a knife blade (not explicitly shown), similar to knife blade 218. Elongated collar 370 has a proximally located gear 373 in meshing engagement with gear 319 of drive member 315 such that rotation of drive member 315 effects rotation of elongate collar 370. The actuation of the knife blade of actuation mechanism 300 via elongate collar 370 is effected in a similar manner as described above with regard to elongate collar 260, and therefore will not be described again with regard to elongate collar 370. Elongate collar 370 includes an internal threadform having a first thread 372 and a second thread 374. The double threadform reduces the amount of plastic required during manufacturing of elongate collar 370.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An actuation mechanism for actuating an electrosurgical end effector, comprising:
   a housing including:

a first drive member;
a second drive member; and
a shroud threadedly engaged to the second drive member; and
a shaft assembly extending distally from the housing, the shaft assembly including:
an elongate collar having an internal threadform extending along a length thereof, the elongate collar operatively coupled to the first drive member such that rotation of the first drive member rotates the elongate collar relative to the housing;
a shaft extending through the elongate collar and having a proximal end and a distal end configured to effectuate movement of a jaw member of an electrosurgical end effector upon axial movement of the shaft relative to the housing, wherein the shroud and the second drive member together define a first longitudinal axis and the shaft defines a second longitudinal axis that is offset from and parallel with the first longitudinal axis;
a collar assembly fixedly disposed about the proximal end of the shaft, the shroud in abutment with the collar assembly such that axial movement of the shroud, via rotation of the second drive member, results in axial movement of the shaft via axial movement of the collar assembly; and
a longitudinal bar axially movable relative to the shaft and including:
a proximal end having an extension engaged to the internal threadform of the elongate collar; and
a distal end configured to be coupled to a knife blade of an electrosurgical end effector;
wherein rotation of the elongate collar axially moves the longitudinal bar relative to the elongate collar to move the knife blade.

2. The actuation mechanism according to claim 1, wherein the first drive member includes a gear, and wherein the elongate collar includes a gear in meshing engagement with the gear of the first drive member.

3. The actuation mechanism according to claim 1, wherein the collar assembly includes:
a proximal collar axially fixed to the shaft, such that the proximal collar moves proximally and distally with the shaft;
a distal collar slidably engaged to the shaft; and
a biasing member interconnecting the proximal collar and the distal collar.

4. The actuation mechanism according to claim 3, wherein the distal collar defines an annular cavity in an outer surface thereof, and the shroud has a protrusion disposed within the annular cavity such that proximal and distal movement of the shroud results in corresponding proximal and distal movement of the collar assembly.

5. The actuation mechanism according to claim 1, wherein the housing further includes:
a first input drive coupler non-rotatably coupled to a proximal end of the first drive member; and
a second input drive coupler non-rotatably coupled to a proximal end of the second drive member.

6. The actuation mechanism according to claim 1, wherein the elongate collar is prevented from moving axially relative to the housing.

7. The actuation mechanism according to claim 1, wherein the shaft includes a longitudinal slot formed therein, the extension of the longitudinal bar being disposed outside of the longitudinal slot such that the shaft and the longitudinal bar are axially movable relative to one another.

8. The actuation mechanism according to claim 1, wherein the housing includes at least one securement member configured to secure the housing to a surgical robotic arm.

9. The actuation mechanism according to claim 1, wherein the shaft assembly further includes a rod axially fixed relative to the housing, the rod extending distally from the housing, through the shaft, and terminating distally at the electrosurgical end effector.

10. An electrosurgical instrument, comprising:
an end effector including:
a pair of opposing jaw members configured to grasp and seal a tissue disposed therebetween; and
a knife blade movably disposable between the pair of opposing jaw members to sever the tissue disposed therebetween; and
an actuation mechanism including:
a housing including:
a drive member;
a drive screw; and
a shroud threadedly engaged to the drive screw; and
a shaft assembly extending distally from the housing, the shaft assembly including:
an elongate collar having an internal threadform extending along a length thereof, the elongate collar operatively coupled to the drive member such that rotation of the drive member rotates the elongate collar relative to the housing;
a shaft extending through the elongate collar and having a proximal end and a distal end in operative communication with one of the pair of opposing jaw members such that movement of the shaft relative to the housing approximates or expands the pair of opposing jaw members, wherein the shroud and the drive screw together define a first longitudinal axis and the shaft defines a second longitudinal axis that is offset from and parallel with the first longitudinal axis;
a collar assembly fixedly disposed about the proximal end of the shaft, the shroud in abutment with the collar assembly such that axial movement of the shroud, via rotation of the drive screw, results in axial movement of the shaft via axial movement of the collar assembly; and
a longitudinal bar axially movable relative to the shaft and including:
a proximal end having an extension engaged to the internal threadform of the elongate collar; and
a distal end coupled to the knife blade;
wherein rotation of the elongate collar axially moves the longitudinal bar relative to the elongate collar to move the knife blade.

11. The electrosurgical instrument according to claim 10, wherein the drive member includes a gear, and wherein the elongate collar includes a gear in meshing engagement with the gear of the drive member.

12. The electrosurgical instrument according to claim 10, wherein the collar assembly includes:
a proximal collar axially fixed to the shaft, such that the proximal collar moves proximally and distally with the shaft;
a distal collar slidably engaged to the shaft; and
a biasing member interconnecting the proximal collar and the distal collar.

13. The electrosurgical instrument according to claim 12, wherein the distal collar defines an annular cavity in an outer surface thereof, and the shroud has a protrusion disposed within the annular cavity such that proximal and distal movement of the shroud results in corresponding proximal and distal movement of the collar assembly.

14. The electrosurgical instrument according to claim 10, wherein the housing further includes:
   a first input drive coupler non-rotatably coupled to a proximal end of the drive member; and
   a second input drive coupler non-rotatably coupled to a proximal end of the drive screw.

15. The electrosurgical instrument according to claim 10, wherein the shaft includes a longitudinal slot formed therein, the extension of the longitudinal bar being disposed outside of the longitudinal slot such that the shaft and the longitudinal bar are axially movable relative to one another.

16. The electrosurgical instrument according to claim 10, wherein the housing includes at least one securement member configured to secure the housing to a surgical robotic arm.

17. The electrosurgical instrument according to claim 10, wherein the shaft assembly further includes a rod axially fixed relative to the housing, the rod extending distally from the housing, through the shaft, and terminating distally at the pair of opposing jaw members.

18. A robotic surgical assembly, comprising:
   a surgical robotic arm;
   an end effector including:
      a pair of opposing jaw members configured to grasp and seal a tissue disposed therebetween; and
      a knife blade movably disposable between the pair of opposing jaw members to sever the tissue disposed therebetween; and
   an actuation mechanism configured to be coupled to the surgical robotic arm, the actuation mechanism including:
      a housing including:
         a first drive member;
         a second drive member;
         a guidepost extending between proximal and distal ends of the housing;
         a first shroud threadedly engaged to the second drive member; and
         a second shroud slidably disposed about the guidepost; and
      a shaft assembly extending distally from the housing, the shaft assembly including:
         an elongate collar operatively having an internal threadform extending along a length thereof, the elongate collar operatively coupled to the first drive member such that rotation of the first drive member rotates the elongate collar relative to the housing;
         a shaft extending through the elongate collar and having a proximal end operatively coupled to the second drive member and a distal end in operative communication with one of the pair of opposing jaw members such that movement of the shaft relative to the housing via rotation of the second drive member approximates or expands the pair of opposing jaw members, wherein the first shroud and the second drive member together define a first longitudinal axis and the shaft defines a second longitudinal axis that is offset from and parallel with the first longitudinal axis;
         a collar assembly fixedly disposed about the proximal end of the shaft, the first and second shrouds in abutment with the collar assembly such that axial movement of the first shroud, via rotation of the second drive member, results in axial movement of the shaft via axial movement of the collar assembly; and
         a longitudinal bar axially movable relative to the shaft and including:
            a proximal end having an extension engaged to the internal threadform of the elongate collar; and
            a distal end coupled to the knife blade;
      wherein rotation of the elongate collar via rotation of the first drive member axially moves the longitudinal bar relative to the elongate collar to move the knife blade.

19. The robotic surgical assembly according to claim 18, wherein the shaft assembly further includes a rod axially fixed relative to the housing, the rod extending distally from the housing, through the shaft, and terminating distally at the pair of opposing jaw members.

* * * * *